(12) United States Patent
Unsai et al.

(10) Patent No.: US 8,208,015 B2
(45) Date of Patent: Jun. 26, 2012

(54) ENDOSCOPE AND ENDOSCOPE APPARATUS

(75) Inventors: Hiroshi Unsai, Hachioji (JP); Seiji Iwasaki, Hachioji (JP); Hiroyuki Nagamizu, Sagamihara (JP); Hiroaki Kagawa, Sagamihara (JP); Hiroshi Ishii, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1289 days.

(21) Appl. No.: 11/974,590

(22) Filed: Oct. 15, 2007

(65) Prior Publication Data

US 2008/0088701 A1    Apr. 17, 2008

(30) Foreign Application Priority Data

Oct. 17, 2006 (JP) .................................. 2006-282946

(51) Int. Cl.
*A62B 1/04* (2006.01)
(52) U.S. Cl. .......................................... 348/65; 348/72
(58) Field of Classification Search ..................... 348/65, 348/72
See application file for complete search history.

(56) References Cited

U.S. PATENT DOCUMENTS

| | | | | |
|---|---|---|---|---|
| 4,882,619 A | * | 11/1989 | Hasegawa et al. | 348/337 |
| 4,919,114 A | * | 4/1990 | Miyazaki | 600/110 |
| 5,088,492 A | * | 2/1992 | Takayama et al. | 600/431 |
| 5,269,289 A | * | 12/1993 | Takehana et al. | 600/109 |
| 5,365,268 A | * | 11/1994 | Minami | 348/76 |
| 5,910,816 A | * | 6/1999 | Fontenot et al. | 348/65 |
| 2006/0238614 A1 | * | 10/2006 | Konno | 348/69 |
| 2010/0079587 A1 | * | 4/2010 | Yoshida | 348/68 |

FOREIGN PATENT DOCUMENTS

| | | |
|---|---|---|
| EP | 0 713 672 A2 | 5/1996 |
| JP | 61-129961 | 6/1986 |
| JP | 11-004456 | 1/1999 |
| JP | 2000-221411 | 8/2000 |

\* cited by examiner

*Primary Examiner* — Firmin Backer
*Assistant Examiner* — Jonathan Bui
(74) *Attorney, Agent, or Firm* — Scully, Scott, Murphy & Presser, P.C.

(57) ABSTRACT

An endoscope in accordance with the present invention provides an endoscope having an image pickup apparatus and including a first connection portion provided on one side surface of a first solid-state image pickup device to connect the first solid-state image pickup device to a first circuit board, and a second connection portion provided on one side surface of a second solid-state image pickup device to connect the second solid-state image pickup device to a second circuit board, the first solid-state image pickup device and the second solid-state image pickup device being arranged in proximity to each other so that a side surface of the first solid-state image pickup device which does not have the first connection portion lies opposite to a side surface of the second solid-state image pickup device which does not have the second connection portion.

9 Claims, 8 Drawing Sheets

ENDOSCOPE AND ENDOSCOPE APPARATUS

This application claims benefit of Japanese Patent Application No. 2006-282946 filed in Japan on Oct. 17, 2006 the contents of which are incorporated by this reference.

BACKGROUND OF THE INVENTION

1. Field of the Invention

The present invention relates to an endoscope and an endoscope apparatus having an image pickup apparatus including two image pickup devices.

2. Description of the Related Art

Image pickup apparatuses having an objective optical system and a solid-state image pickup device (hereinafter referred to as a CCD) have been widely used. The image pickup apparatus which can obtain high quality images from picked-up observed image is naturally desired and for some apparatuses in which the image pickup apparatus is installed, the image pickup apparatus is desired to have a reduced size.

In particular, in an endoscope having the image pickup apparatus in a distal end portion of an insertion portion, although the structure of the distal end portion varies among different types of endoscopes, mostly the image pickup apparatus and a light guide occupies a large part of the volume of the space in the distal end portion. Consequently, the sizes of these two members substantially determine the diameter of the distal end portion of the endoscope. Thus, a reduction in the size of the image pickup apparatus enables a reduction in the diameter of the distal end portion of the insertion portion and in the diameter of the insertion portion itself.

A part of the image pickup apparatus in which the CCD is mounted has the largest size in the whole image pickup apparatus. Consequently, determining the size of the CCD substantially determines the diameter of the distal end potion of the insertion portion. Therefore, for a reduction in the size of the image pickup apparatus, the configuration of the part with the CCD mounted therein must be taken into account.

Further, as described above, the image pickup apparatus needs not only to have a reduced size but also to be able to pick up high-quality images. A common method for improving the quality of images picked up by the image pickup apparatus is to increase the number of pixels in the CCD.

However, an increased number of pixels necessarily increase the size of the CCD, making it difficult to reduce the diameter of the distal end portion of the insertion portion. That is, there is a tradeoff relationship between the reduced diameter of the distal end portion and the improved image quality.

A well-known method for achieving both the reduced diameter of the distal end portion and the improved image quality is a multiple CCD structure in which a plurality of CCDs are used to improve the image quality. With the diameter of the distal end portion adjusted to be equivalent to that in a single CCD structure, an image pickup apparatus with a double CCD structure using two CCDs (hereinafter referred to as a double image pickup apparatus) is suitable for the endoscope.

For example, a single-plate image pickup apparatus with a single CCD structure using a single CCD has color filters for red, green, and blue or cyan, magenta, and yellow in the CCD so that colors can be formed using four pixels.

On the other hand, in a double image pickup apparatus using two CCDs, one of the CCDs is equipped with a prism coated so as to reflect green, while allowing red and blue to pass through and red color filters and blue color filters provided in stripes in a direction in which red and blue pass through the filters. The other CCD has black and white color filters or green color filters in a direction in which green is reflected. Thus, colors are formed using two pixels in the CCDs. That is, the image quality can be improved without the need to increase the number of pixels.

A conventional technique for such a double image pickup apparatus is disclosed in, for example, Japanese Patent Laid-Open No. 2000-221411 or No. 61-129961. Japanese Patent Laid-Open No. 2000-221411 discloses a technique for an electronic endoscope apparatus having a double image pickup apparatus with two CCDs; Japanese Patent Laid-Open No. 2000-221411 intends to provide an image pickup apparatus which provides a higher quality than a single-plate image pickup apparatus with one CCD and which is more inexpensive than a triple image pickup apparatus with three CCDs.

Japanese Patent Laid-Open No. 61-129961 discloses a technique for a double solid-state image pickup apparatus for an electronic still camera which is configured as a double image pickup apparatus described above and specifically in which one of the CCDs is located parallel to an incident optical path, whereas the other CCD is located perpendicular to the incident optical path.

SUMMARY OF THE INVENTION

In short, in an endoscope according to the present invention including a prism having a first prism and a second prism that are joined together so as to divide and emit incident light having passed through an objective optical system into two optical paths, a first solid-state image pickup device that receives light emitted by the prism after being reflected by a interface between the first prism and the second prism, and a second solid-state image pickup device that receives light emitted by the prism after passing through the first and second prisms, the endoscope comprises a first connection portion provided on one side surface of the first solid-state image pickup device to connect the first solid-state image pickup device to a first circuit board, and a second connection portion provided on one side surface of the second solid-state image pickup device to connect the second solid-state image pickup device to a second circuit board, the first solid-state image pickup device and the second solid-state image pickup device being arranged in proximity to each other so that a side surface of the first solid-state image pickup device which does not have the first connection portion lies opposite to a side surface of the second solid-state image pickup device which does not have the second connection portion.

In brief, in an endoscope apparatus according to the present invention which comprises an endoscope including a prism having a first prism and a second prism that are joined together so as to divide incident light having passed through an objective optical system into two optical paths, a first solid-state image pickup device that receives light emitted by the prism after being reflected by a interface between the first prism and the second prism, and a second solid-state image pickup device that receives light emitted by the prism after passing through the first and second prisms, the endoscope apparatus comprises a first connection portion provided on one side surface of the first solid-state image pickup device to connect the first solid-state image pickup device to a first circuit board, and a second connection portion provided on one side surface of the second solid-state image pickup device to connect the second solid-state image pickup device to a second circuit board, the first solid-state image pickup device and the second solid-state image pickup device being arranged in proximity to each other so that a side surface of the first solid-state image pickup device which does not have the first connection portion lies opposite to a side surface of the second solid-state image pickup device which does not have the second connection portion.

The above and other objects, features and advantages of the invention will become more clearly understood from the following description referring to the accompanying drawings.

DETAILED DESCRIPTION OF THE PREFERRED EMBODIMENTS

Embodiment 1

Embodiments of the present invention will be described below with reference to the drawings.

Figure 1:
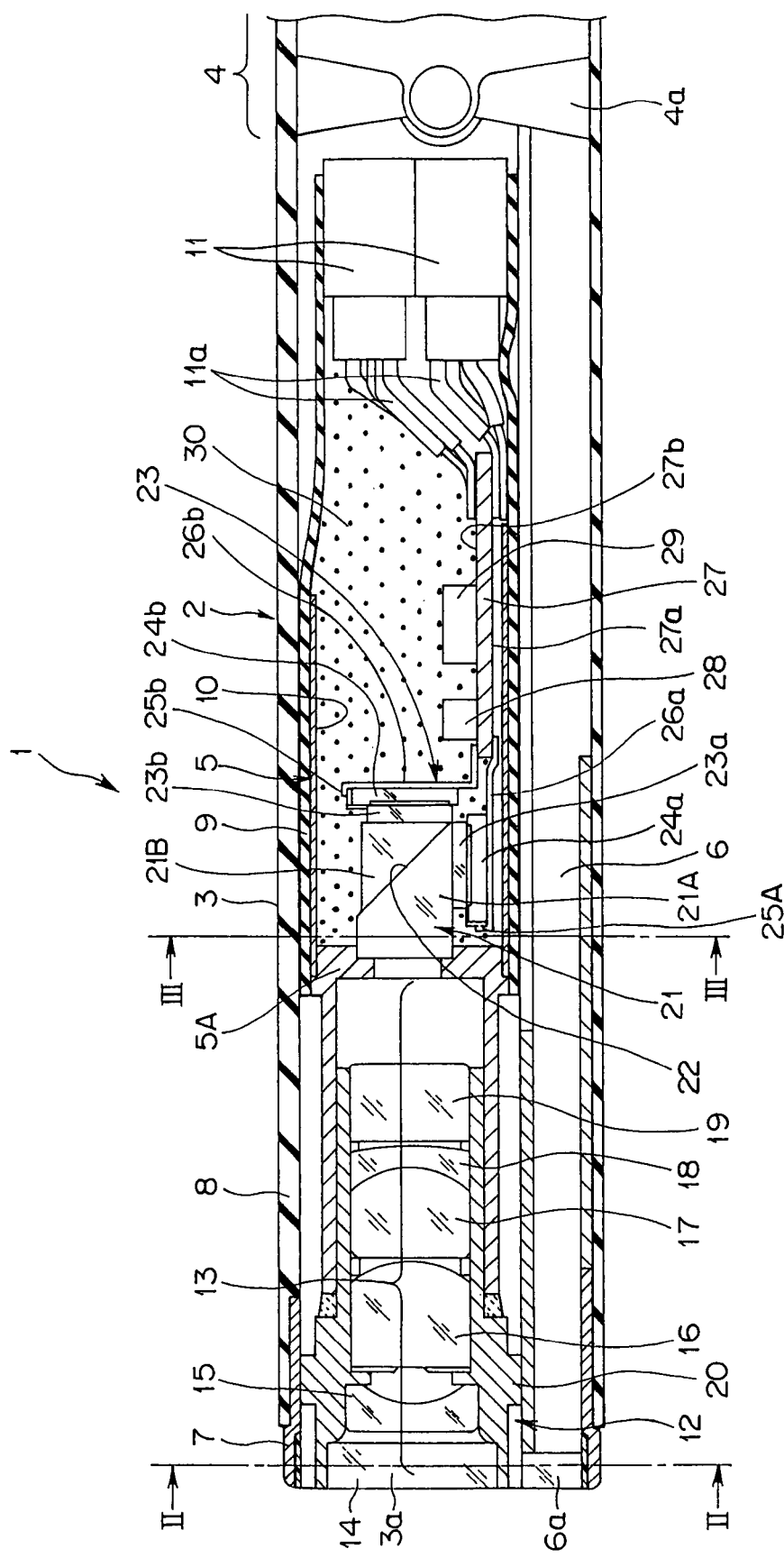
FIG. 1 is a sectional view of a distal end portion of an endoscope in accordance with Embodiment 1 of the present invention.
Figure 2:
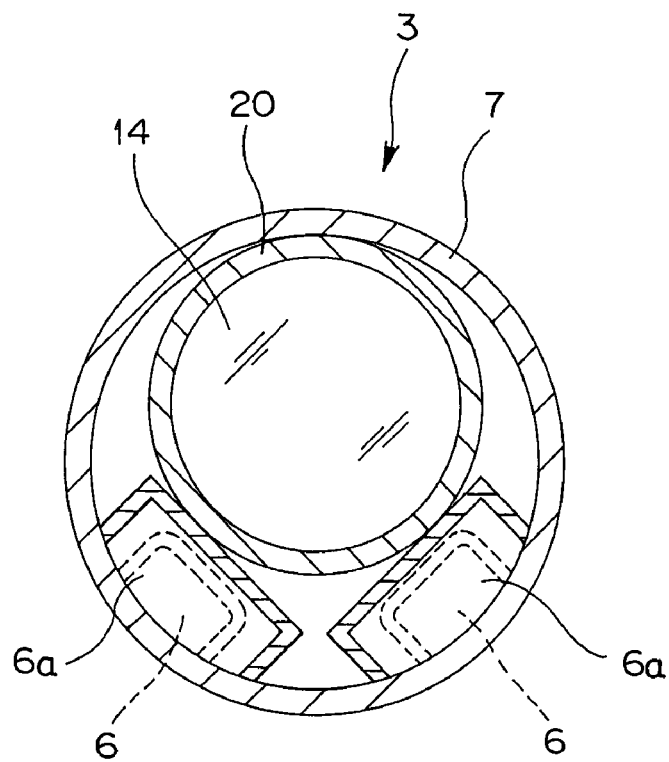
FIG. 2 is a sectional view of the distal end portion along line II-II in FIG. 1.
Figure 3:
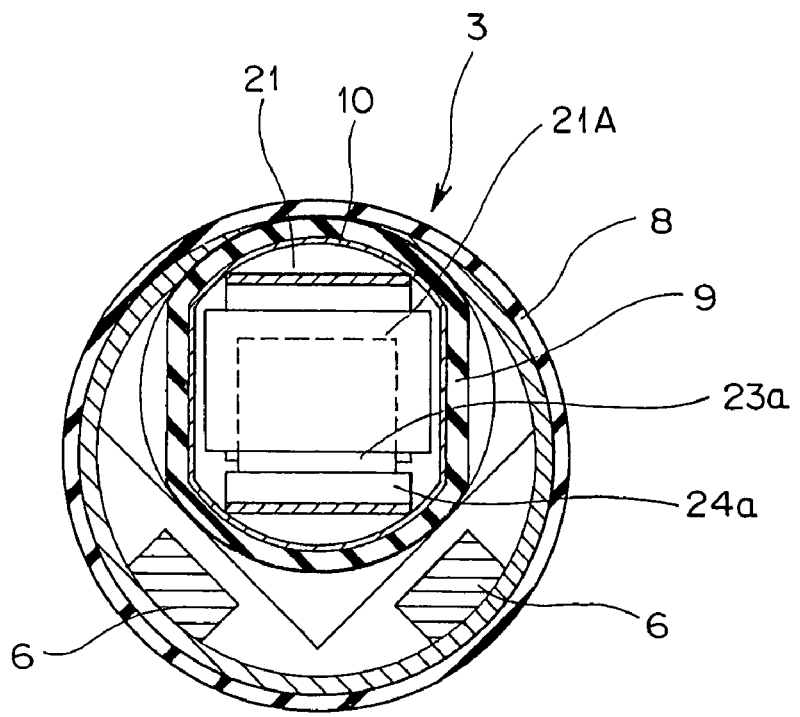
FIG. 3 is a sectional view of the distal end portion along line III-III in FIG. 1.

FIGS. 1 to 7 relate to Embodiment 1 of the present invention. FIG. 1 is a sectional view of a distal end portion of an endoscope in accordance with Embodiment 1 of the present invention. FIG. 2 is a sectional view of the distal end portion taken along line II-II in FIG. 1. FIG. 3 is a sectional view of the distal end portion taken along line III-III in FIG. 1.

Figure 4:
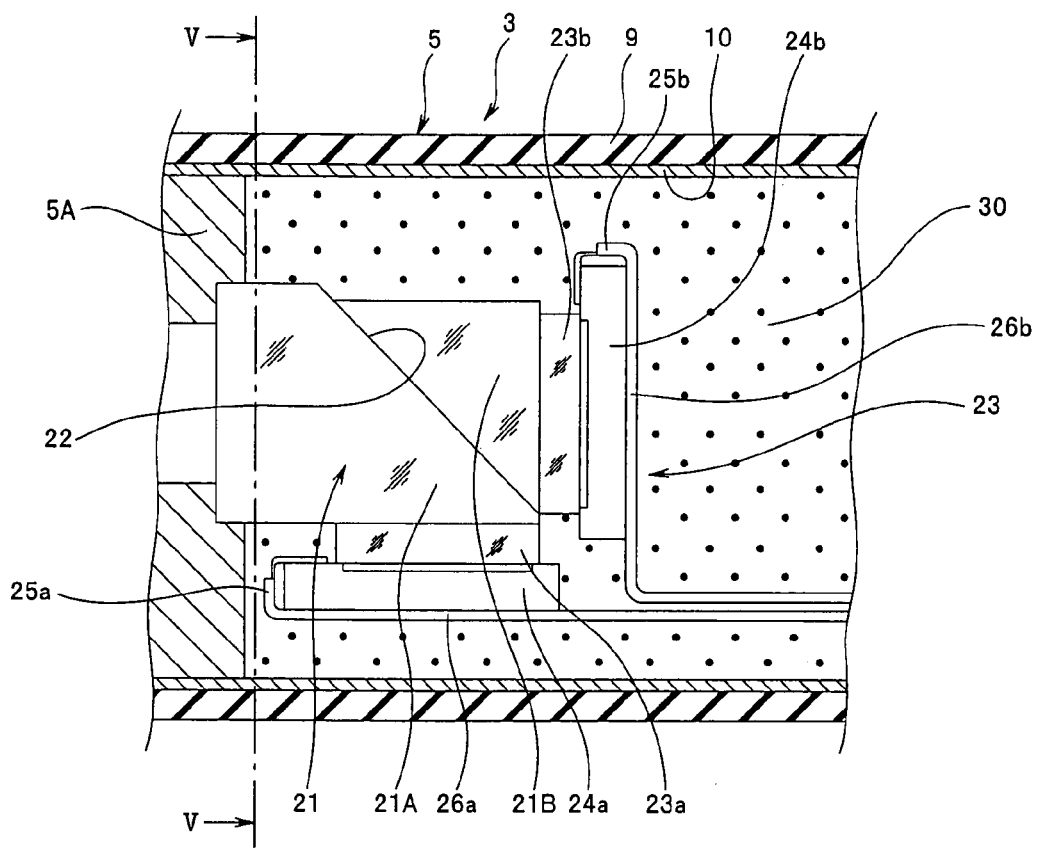
FIG. 4 is a partial sectional view of the distal end portion showing in enlargement a part of an image pickup apparatus in FIG. 1.
Figure 5:
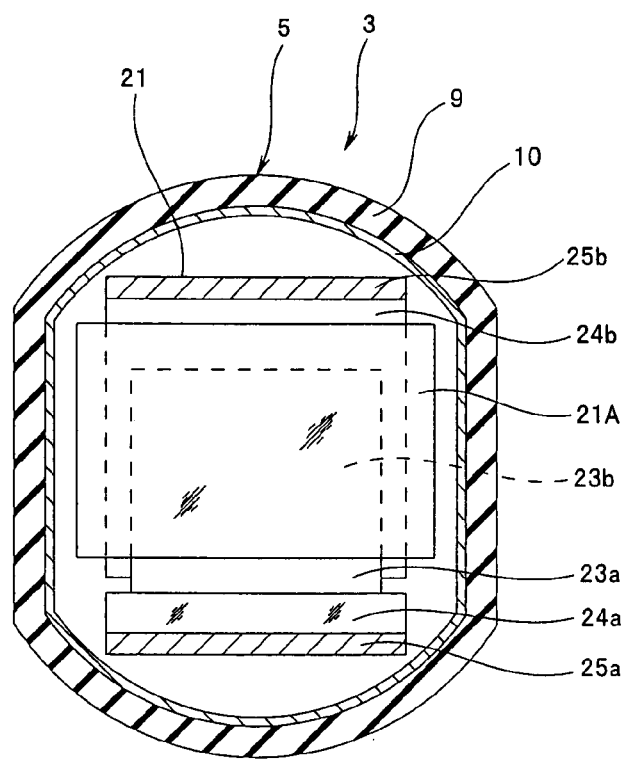
FIG. 5 is a sectional view showing the distal end portion taken along line V-V in FIG. 4.
Figure 6:
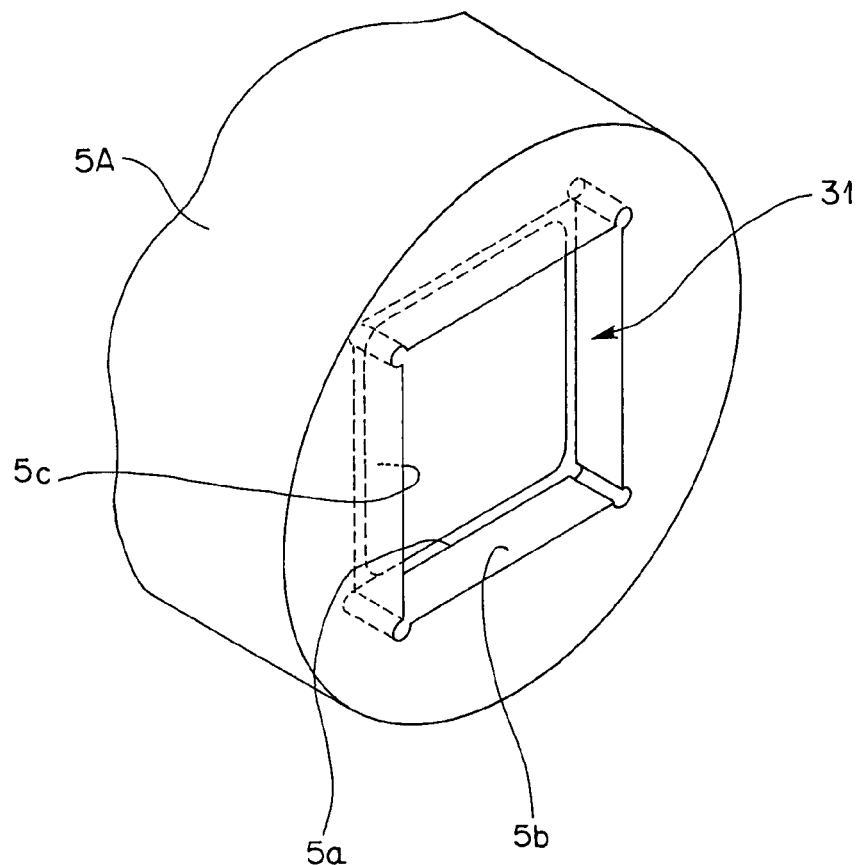
FIG. 6 is a partial perspective view showing the configuration of a prism frame to which a prism is mounted.
Figure 7:
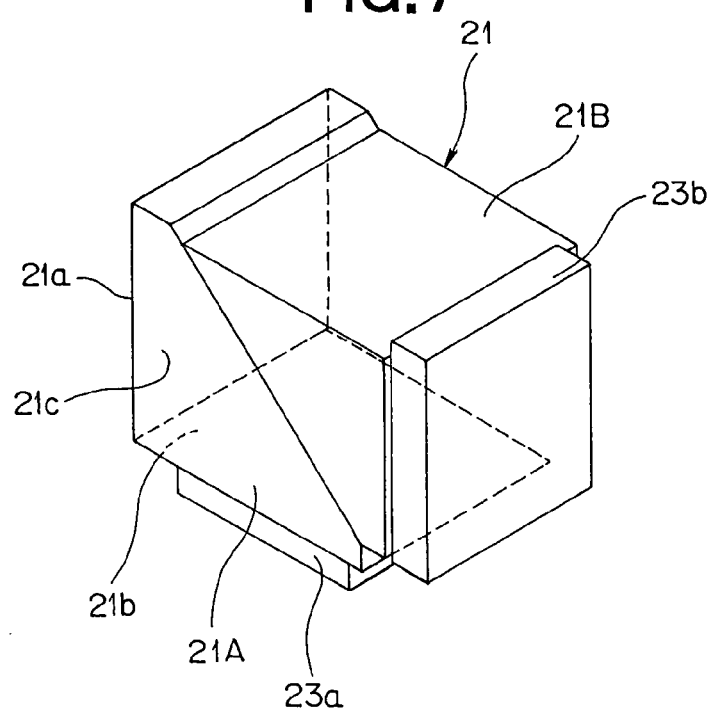
FIG. 7 is a perspective view showing the configuration of a prism fixed to the prism frame in FIG. 6.

FIG. 4 is a partial sectional view of the distal end portion showing in enlargement a part of an image pickup apparatus in FIG. 1. FIG. 5 is a sectional view of the distal end portion taken along line V-V in FIG. 4. FIG. 6 is partial perspective view showing the configuration of a prism frame on which a prism is mounted. FIG. 7 is a perspective view showing the configuration of the prism mounted on the prism frame.

As shown in FIG. 1, an endoscope 1 in accordance with Embodiment 1 is composed of an elongate insertion portion 2 that can be freely inserted into a body cavity or the like, an operation portion (not shown) connected to a rear end of the insertion portion 2, a universal cord portion extended from the operation portion, and a scope connector portion provided at an end portion of the universal code portion and releasably connected to a light source device.

In addition to the endoscope 1, an endoscope apparatus may be provided with a light source device (not shown) that provides illumination light by connecting to the endoscope 1, for example, a video processor (not shown) connected to the endoscope 1 via a scope cable that executes signal processing on a first solid-state image pickup device 24a and a second image pickup apparatus 24b both provided in an image pickup apparatus 5 described below and contained in the endoscope 1, and a color monitor (not shown) that displays video signals input via a monitor cable connected to the video processor.

The insertion portion 2 has a distal end portion 3 in which the image pickup apparatus 5 is provided, a bending portion 4 freely bendable formed at a rear end of the distal end portion 3, and an elongate flexible tube portion (not shown) extending from the rear end of the bending portion 4 to a front end of the operation portion.

A light guide 6 for transmitting illumination light is placed so as to extend through the insertion portion 2, the operation portion (not shown), and the universal cord portion as shown in FIGS. 1 to 3. The light guide 6 has a rear end positioned in the scope connector portion so as to transmit illumination light provided by a lamp inside the light source device. The light guide 6 emits the illumination light forward from a distal end surface which is fixed to an illumination window 6a of the distal end portion 3, to illuminate a subject such as an affected part. Two light guides 6 are provided as shown in, for example, FIGS. 2 and 3.

A subject image illuminated with the illumination light is formed in the first and second solid-state image pickup devices 24a, 24b, arranged at an image formation position and described below, via an objective optical system unit 12 mounted to an observation window 3a located adjacent to the illumination window 6a and via a prism 21 described below. The subject image is then subjected to a photoelectric conversion by the first and second solid-state image pickup devices 24a and 24b.

As described below, a signal cable 11 is connected to each of the first and second solid-state image pickup devices 24a and 24b. Although not shown, the signal cable 11 is connected to a scope cable via a noise reducer (not shown) housed in the scope connector section, the scope cable is connected to the video processor.

Now, with reference to FIGS. 1 to 7, description will be given of the configuration of the distal end portion 3 of the endoscope 1 and the image pickup apparatus 5 in the distal end portion 3.

As shown in FIG. 1, the distal end portion 3 has the image pickup apparatus 5, the two light guides 6, and a distal end frame 7.

The image pickup apparatus 5 has the objective optical system unit 12, a prism optical system unit (hereinafter referred to as a prism) 21 disposed behind the objective optical system unit 12, and an image pickup unit 23 disposed in the vicinity of the prism 21.

The objective optical system unit 12 comprises an objective lens group 13 made of a plurality of lenses and an objective lens frame 20 that internally holds the objective lens group. The objective optical system unit 12 is held in the distal end portion 3 by fitting the objective lens frame 20 into the distal end frame 7.

The objective lens group 13 has, for example, an objective lens 14 as a first lens, a second lens 15, a third lens 16, a fourth lens 17, a fifth lens 18, a sixth lens, and a diaphragm (not shown) and the like. However, the present invention is not limited to this configuration.

A prism frame 5A is fittingly installed at a proximal end of the objective lens frame 20. The image pickup unit 23 is held by the objective optical system unit 12 via the prism frame 5A and the prism 21, fixed to the prism frame 5A.

Now, with reference to FIGS. 6 and 7, description will be given of a method for fixing the prism 21 to the prism frame 5A.

As shown in FIG. 6, a fitting slot 31 is formed in the proximal end surface of the prism frame 5A and shaped like a square so that the prism 21 can be fittingly installed in the fitting slot 31. An abutting surface 5a is formed along an edge of the fitting slot 31 which is closer to the objective optical system unit 12. Other abutting surfaces 5b and 5c are formed along the inner periphery of the fitting slot 31 and adjacent to the abutting surface 5a.

On the other hand, the prism 21 has a first prism 21A described below in detail. The first prism 21A has an abutting surface 21a abutting against the abutting surface 5a of the fitting slot 31, an abutting surface 21b abutting against the abutting surface 5b, and an abutting surface 21c abutting against the abutting surface 5c.

In the present embodiment, the prism 21 and the prism frame 5A are adhesively fixed together by fitting the first prism 21A of the prism 21 into the fitting slot 31 in the prism frame 5A.

The surfaces of the prism 21 abut against the corresponding surfaces of the prism frame 5A on the basis of the three abutting surfaces 21a to 21c of the first prism 21A and the three abutting surfaces 5a to 5c of the prism frame 5A so that the optical axes of the prism 21 and the prism frame 5A coincide with the optical axis of the objective optical system unit 12. In this state, the first prism 21A is adhesively fixed in the fitting slot 31.

The prism 21 fixed to the prism frame 5A divides incident light having passed through the objective optical system unit 12 into two optical paths and emits the light along these optical paths. The prism 21 has a first prism 21A, a second prism 21B joined to the first prism 21A, and a green reflection coat layer (also referred to as a dichroic coat layer) 22 disposed at a junction interface at which the first prism 21A and the second prism 21B overlap.

To form the green reflection coat layer 22 at the junction interface at which the first prism 21A and the second prism 21B overlap, a reflection film is formed on an inclined surface of the first prism 21A. The green reflection layer 22 is characterized by reflecting incident green (G) light, while allowing incident red (R) light and incident blue (B) light to pass through.

A cover glass 23a and the first solid-state image pickup device 24a are arranged in this order on and adhesively fixed to an emission surface of the first prism 21A toward which light is substantially perpendicularly reflected by the green reflection coat layer 22 of the first prism 21A; the cover glass 23a constitutes a part of the image pickup unit 23, and the first solid-state image pickup device 24a reproduces a luminance signal (Y signal).

A cover glass 23b and the second solid-state image pickup device 24b are arranged in this order on and adhesively fixed to a back side (emission surface) of the first prism 21A toward which light is emitted after passing through the green reflection coat layer 22 of the first prism 21A; the cover glass 23b constitutes a part of the image pickup unit 23, and the second solid-state image pickup device 24b reproduces color signals (R and B signals).

For example, an optical adhesive is used to bond the first prism 21A to the second prism 21B and to bond the prism 21 to the cover glasses 23a and 23b. These components are fixed together with the film thickness of the optical adhesive adjusted. The first solid-state image pickup device 24a and the second solid-state image pickup device 24b are adjusted so that the first prism 21A has the same optical length as that of the second prism 21B.

The image pickup unit 23 has the cover glasses 23a and 23b, the first and second solid-state image pickup devices 24a and 24b, and a circuit board 27 on which electric parts such as a capacitor 29 and an IC circuit 28 are mounted and which has a first circuit board 27a and a second circuit board 27b arranged on a top surface and a bottom surface, respectively.

In this case, the first circuit board 27a is provided on the bottom surface of the circuit board 27. The second circuit board 27b is provided on the top surface of the circuit board 27. The first and second circuit boards 27a and 27b need not be provided on the top and bottom surfaces of the one circuit board 27 as shown in FIG. 1. The circuit board 27 may be vertically divided into two pieces so that the first and second circuit boards 27a and 27b can be provided on the respective pieces.

The first and second circuit boards 27a and 27b are electrically connected to the first and second solid-state image pickup devices 24a and 24b via a first transmission draw-out portion 25a and a second transmission draw-out portion 25b constituting a first connection portion and a second connection portion, respectively, and via leads 26a and 26b.

Here, the circuit board 27 has what is called a TAB (Tape Automated Bonding) structure. Although not shown, the circuit board 27 comprises a polyimide base member and a conductor pattern made of a copper foil provided on the polyimide base member.

A part of the conductor pattern (not shown) is extended from an end of the polyimide base member and electrically connected to the leads 26a and 26b to transmit and receive signals to and from the first and second solid-state image pickup devices 24a and 24b.

As shown in FIGS. 1 and 4, the leads 26a and 26b are electrically connected to the first and second solid-state image pickup devices 24a and 24b, respectively, by the first and second transmission draw-out portions 25a and 25b, constituting the first and second connection portions.

The first transmission draw-out portion 25a, constituting the first connection portion, is provided on one side surface of the first solid-state image pickup device 24a to electrically connect the first solid-state image pickup device 24a to the first circuit board 27a of the circuit board 27.

The second transmission draw-out portion 25b, constituting the second connection portion, is provided on one side surface of the second solid-state image pickup device 24b to electrically connect the second solid-state image pickup device 24b to the second circuit board 27b of the circuit board 27.

The first and second transmission draw-out portions 25a and 25b use, for example, solder to electrically connect the leads 26a and 26b to electric contact portions of the first and second solid-state image pickup devices 24a and 24b, specifically, electric contact portions or transmission portions electrically connected to effective pixels. However, the connection is not limited to the solder or the like. Other means may be used for the electric connections.

Signal lines 11a in the signal cable 11 are electrically connected to the first and second circuit boards 27a and 27b, respectively.

The first solid-state image pickup device 24a receives light emitted by the prism 21 after being reflected by the green reflection coat layer 22 located at the interface between the first prism 21A and the second prism 21B. The second solid-state image pickup device 24b receives light emitted by the prism 21 after passing through the first and second prisms 21A and 21B.

Although not shown, red (R) color filters and blue (B) color filters are provided on a light receiving surface of the second solid-state image pickup device 24b in stripes. The second solid-state image pickup device 24b is thus configured to reproduce color signals (R and B signals).

No color filter is provided on a light receiving surface of the first solid-state image pickup device 24a. The first solid-state image pickup device 24a is configured to reproduce a luminance signal (Y signal).

The first and second solid-state image pickup devices 24a and 24b are composed of image sensors such as CCDs (Charge Coupled Devices) or CMOSs (Complementary Metal Oxide Semiconductors). The first solid-state image pickup device 24a and the second solid-state image pickup device 24b have substantially similar configurations except for the presence of color filters.

A reinforcing frame 10 is fittingly installed around the outer periphery of a proximal end of the prism frame 5A, as shown in FIGS. 1 and 4. The reinforcing frame 10 is characterized by preventing an external force from being applied to the image pickup apparatus 5 during a bending operation.

The reinforcing frame 10 exerts the same effect as that of a shield member. That is, in order to inhibit unwanted radiation, the reinforcing frame 10 is extended to the vicinity of a distal end portion of the signal cable 11 fixed so as to cover the prism 21, the outer periphery of the first and second solid-state image pickup devices 24a and 24b. An adhesive 30 is filled between the reinforcing frame 10 and the prism 21 and the image pickup unit 23 to firmly fix the prism 21 and the image pickup unit 23.

As shown in FIG. 5, the reinforcing frame 10 is shaped to have the same gap on the right and left of or above and below the prism 21 so that fixing portions of the cover glasses 23a and 23b which are fixed to the prism 21 by the optical adhesive are separated from the prism 21 by a force resulting from expansion or hardening shrinkage of the adhesive 30. The reinforcing frame 10 is shaped like a circle or an ellipsis taking into account a reduction in the diameter of the distal end portion 3 of the insertion portion 2 and processability of the distal end frame 7.

The proximal end portion of the prism frame 5A and the reinforcing frame 10 have a cover member 9 for insulation. The cover member 9 covers and seals an area from the proximal end portion of the prism frame 5A to the distal end portion of the signal cable 11.

A bending first piece 4a constituting a bending tube is connected to the proximal end of the distal end portion 3. A rubber cover member 8 extending to the distal end portion 3 and the bending portion 4 is provided around the outer periphery of the bending first piece 4a. A distal end portion of the cover member 8 is connected to a proximal end portion of the distal end frame 7. The distal end portion 3 is thus sealed.

Now, with reference to FIGS. 1 to 5, description will be given of an arrangement effective for reducing the size of the image pickup apparatus 5 in the endoscope 1 in accordance with the present embodiment.

That is, in the image pickup apparatus 5 in the endoscope 1 in accordance with the present embodiment, as shown in FIGS. 1 and 4, the first solid-state image pickup device 24a and the second solid-state image pickup device 24b are arranged in proximity to each other so that a side surface of the first solid-state image pickup device 24a which does not have the first transmission draw-out portion 25a, constituting the first connection portion, lies opposite to a side surface of the second solid-state image pickup device 24b which does not have the second transmission draw-out portion 25b, constituting the second connection portion.

The first transmission draw-out portion 25a and the second transmission draw-out portion 25b are arranged away from each other (see FIG. 5), so that the first solid-state image pickup device 24a and the second solid-state image pickup device 24b are arranged in different directions.

That is, in connection with the configuration of the endoscope 1, the light guides 6 are installed on the right and left sides and the square prism 21 and image pickup unit 23 are installed in the insertion portion 2 as shown in FIGS. 2 and 3. A space is thus created at the top and bottom.

Here, since the first transmission draw-out portion 25a and the second transmission draw-out portion 25b are arranged away from each other in different directions, the first solid-state image pickup device 24a and the second solid-state image pickup device 24b can effectively utilize the spaces. This enables a size reduction.

Moreover, the first prism 21A and first solid-state image pickup device 24a and the second prism 21B and second solid-state image pickup device 24b are arranged substantially symmetrically with respect to the green reflection coat layer 22, the interface (lamination surface) between the first and second prisms 21A and 21B.

In this case, available effective pixels in the first solid-state image pickup device 24a have the same relative positions as those in the second solid-state image pickup device 24b. Further, the first and second solid-state image pickup devices 24a and 24b are positioned so that the optical axis of the objective optical system unit 12 coincides with the center of the first and second solid-state image pickup devices 24a and 24b (see FIG. 4).

Consequently, in this configuration, the first solid-state image pickup device 24a and the second solid-state image pickup device 24b are arranged in proximity to each other so that the side surface of the first solid-state image pickup device 24a which does not have the first transmission draw-out portion 25a, constituting the first connection portion, lies opposite to the side surface of the second solid-state image pickup device 24b which does not have the second transmission draw-out portion 25b, constituting the second connection portion. This enables the first solid-state image pickup device 24a and the second solid-state image pickup device 24b to be disposed as close to each other as possible in a direction perpendicular to the direction of the optical axis of the objective optical system unit 12.

That is, the heights of the prism 21 and image pickup unit 23, constituting the image pickup apparatus 5, can be reduced in the direction perpendicular to the direction of the optical axis of the objective optical system unit 12. This enables a reduction in the size of the image pickup apparatus 5.

Now, the working of the endoscope 1 configured as described above will be described.

In the image pickup apparatus 5 in the endoscope 1 configured as described above, the first solid-state image pickup device 24a and the second solid-state image pickup device 24b are arranged in proximity to each other so that the side surface of the first solid-state image pickup device 24a which does not have the first transmission draw-out portion 25a, constituting the first connection portion, lies opposite to the side surface of the second solid-state image pickup device 24b which does not have the second transmission draw-out portion 25b, constituting the second connection portion.

Thus, an image formed by the first solid-state image pickup device 24a corresponds to a lateral inversion of an image formed by the second solid-state image pickup device 24b. Image pickup signals resulting from photoelectric conversion by the first and second solid-state image pickup devices 24a and 24b are supplied to the video processor (not shown) via the first and second circuit boards 27a and 27b of the circuit board 27 and via the signal cable 11. The video processor synthesizes an image obtained by the first solid-state image pickup device 24a with a video signal obtained by the second solid-state image pickup device 24b as required, while inverting the image obtained by the first solid-state image pickup device 24a.

The synthesized video signal is inputted to a color monitor via a monitor cable connected to the video processor. As a result, an image based on the video signal is displayed.

Consequently, as described above, with the image pickup apparatus 5 in the endoscope 1 in accordance with present embodiment, an image obtained by laterally inverting an image obtained by the second solid-state image pickup device 24b is formed on the first solid-state image pickup device 24a.

Thus, with a laterally inverted image, the first and second solid-state image pickup device 24a and 24b execute a data transferring process such that the transfer is performed in a horizontal direction; data in downwardly adjacent scan line is sequentially transferred. This enables image processing to be executed as required while reading image data, allowing an image generating process to be executed in real time without any time lag.

The present embodiment can therefore reduce the size of the whole image pickup apparatus while inexpensively maintaining a high image quality inherent in the double image pickup apparatus, using the simple configuration. The present embodiment can also reduce the size of the image pickup apparatus and thus the size of the distal end portion of the insertion portion.

Embodiment 2

Figure 8:
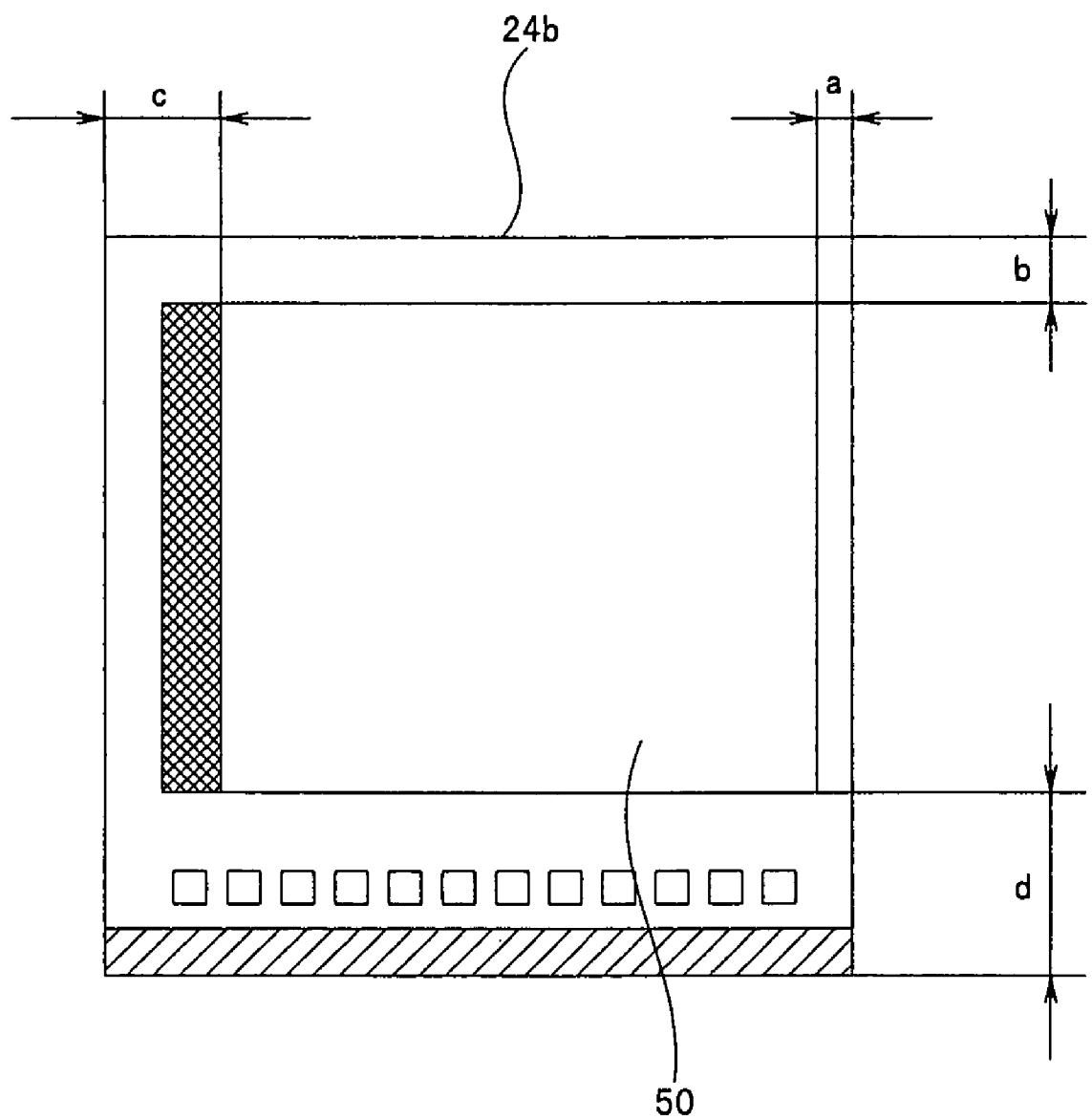
FIG. 8 is a plan view showing the configuration of a second solid-state image pickup device provided in an image pickup apparatus in an endoscope in accordance with Embodiment 2 of the present invention, as viewed from the front of a distal end portion.

FIG. 8 is a plan view showing the configuration of a second solid-state image pickup device provided in an image pickup apparatus in an endoscope in accordance with Embodiment 2 of the present invention, as viewed from the front of a distal end portion. In Embodiment 2, shown in FIG. 8, components similar to those of the image pickup apparatus 5 in the endoscope 1 in accordance with Embodiment 1 are denoted by the same reference numerals and will not be described below. Description will be given below of only the components different from those of the image pickup apparatus 5 in the endoscope 1 in accordance with Embodiment 1.

In the image pickup apparatus 5 in the endoscope 1 in accordance with Embodiment 2, the side surfaces of the first and second solid-state image pickup devices 24a and 24b which do not have the first and second transmission draw-out portions 25a and 25b, respectively, are arranged in proximity to each other and configured to minimize the distance from the effective pixel area to outer peripheral end of each of the first and second solid-state image pickup devices 24a and 24b.

Specifically, when the first and second solid-state image pickup devices 24a and 24b shown in FIG. 8 are used, the distance from the effective pixel area 50 to outer peripheral end of each of the solid-state image pickup devices 24a and 24b varies depending on the direction.

For example, as shown in FIG. 8, in the first and second solid-state image pickup devices 24a and 24b, the distance from the effective pixel area 50 to the right end of the figure is defined as a. The distance from the effective pixel area 50 to the upper end of the figure is defined as b. The distance from the effective pixel area 50 to the left end of the figure is defined as c. The distance from the effective pixel area 50 to the lower end of the figure is defined as d. The distances a to d have the relationship a<b<c<d.

The first and second solid-state image pickup devices 24a and 24b are arranged so that the side surfaces of first and second solid-state image pickup devices 24a and 24b which have the shortest distance a lie in proximity to each other. This enables a reduction in the size of the image pickup unit 23 in a direction perpendicular to the direction of the optical axis of the objective optical system unit 12. This makes it possible to reduce the size of the image pickup apparatus 5 and the diameter of the distal end portion 3 of the insertion portion 2.

In Embodiment 2, if the vertical direction of an image does not match between the first solid-state image pickup device 24a and the second solid-state image pickup device 24b, the video processor may internally execute image processing required to match the vertical direction of the image between the first solid-state image pickup device 24a and the second solid-state image pickup device 24b. The other configuration and working of Embodiment 2 are similar to those of Embodiment 1.

Therefore, Embodiment 2 not only exerts effects similar to those of Embodiment 1 but can also reduce the size of the image pickup unit 23 in the direction perpendicular to the direction of the optical axis of the objective optical system unit 12. This makes it possible to reduce the size of the image pickup apparatus 5 and the diameter of the distal end portion 3 of the insertion portion 2.

Embodiment 3

Figure 9:
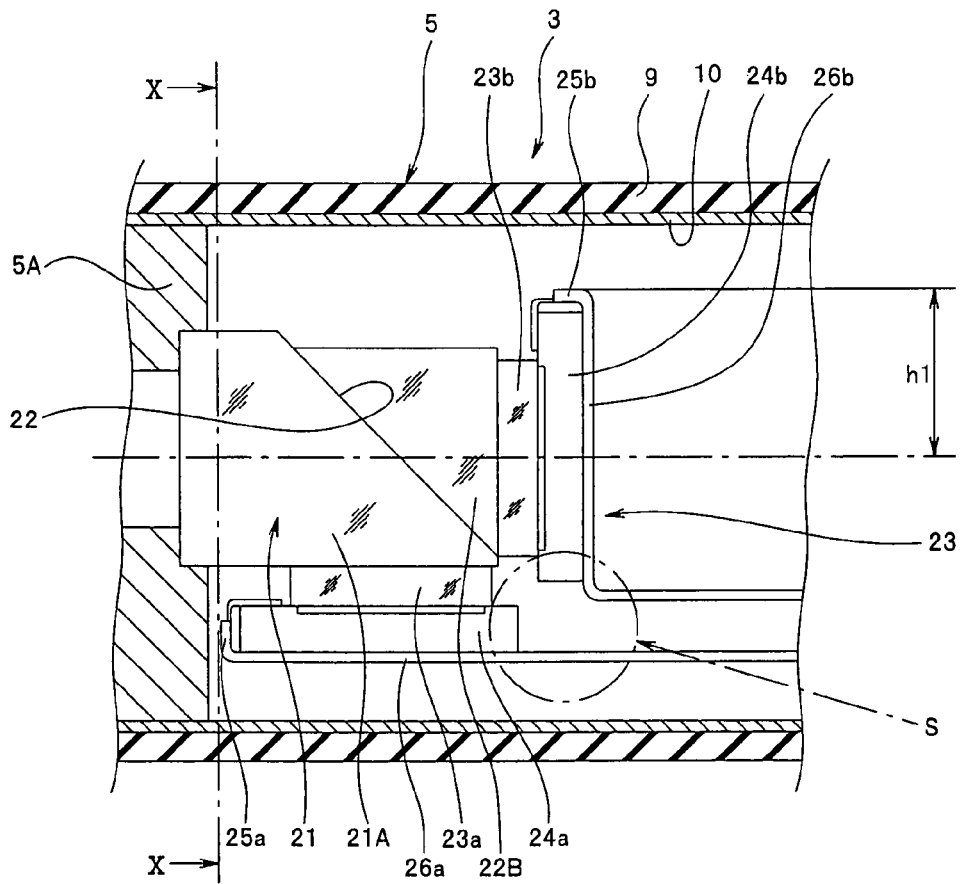
FIG. 9 is a partly enlarged sectional view showing a part of a conventional image pickup apparatus, that is, a distal end portion of the image pickup apparatus, and illustrating problems with the configuration of the image pickup apparatus.
Figure 10:
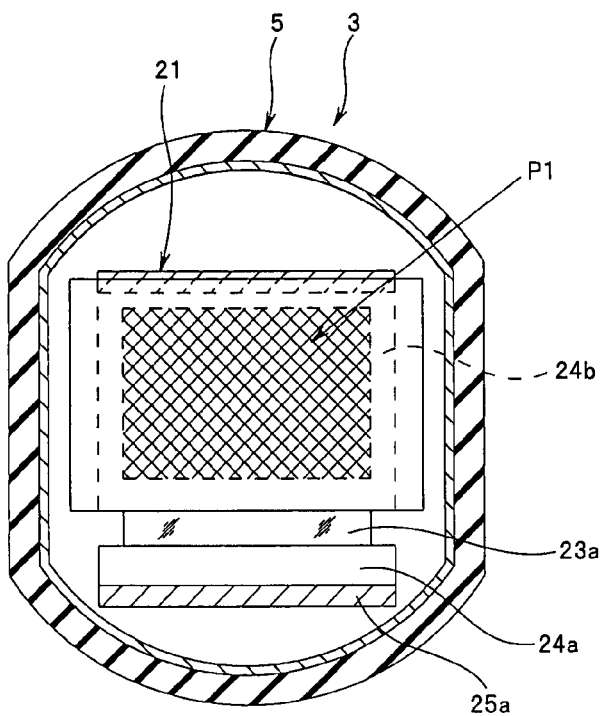
FIG. 10 is a partial sectional view of the distal end portion taken along line X-X in FIG. 9.
Figure 11:
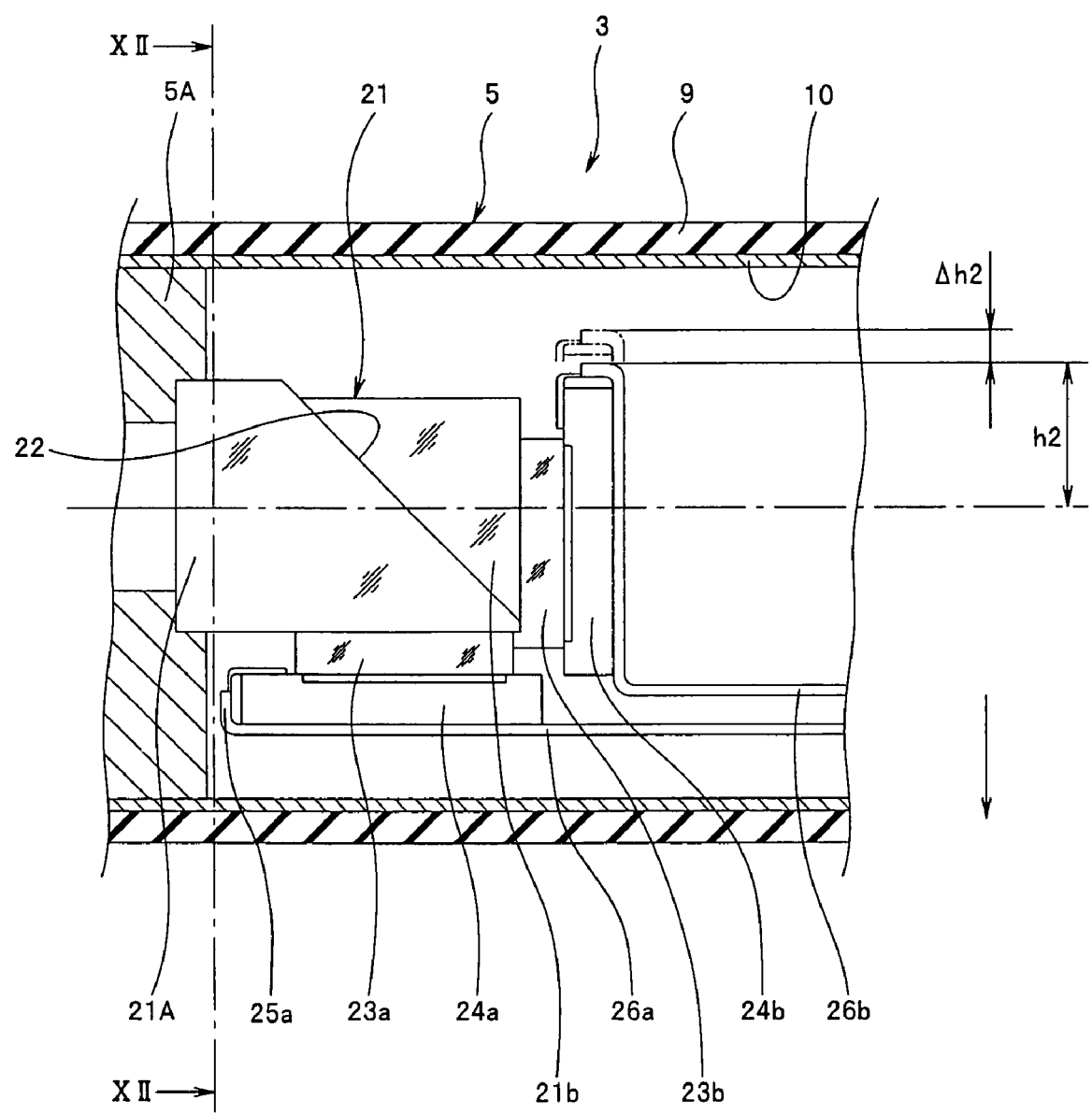
FIG. 11 is an enlarged partial sectional view of a part of an image pickup apparatus in an endoscope in accordance with Embodiment 3 of the present invention, that is, a distal end portion of the image pickup apparatus.
Figure 12:
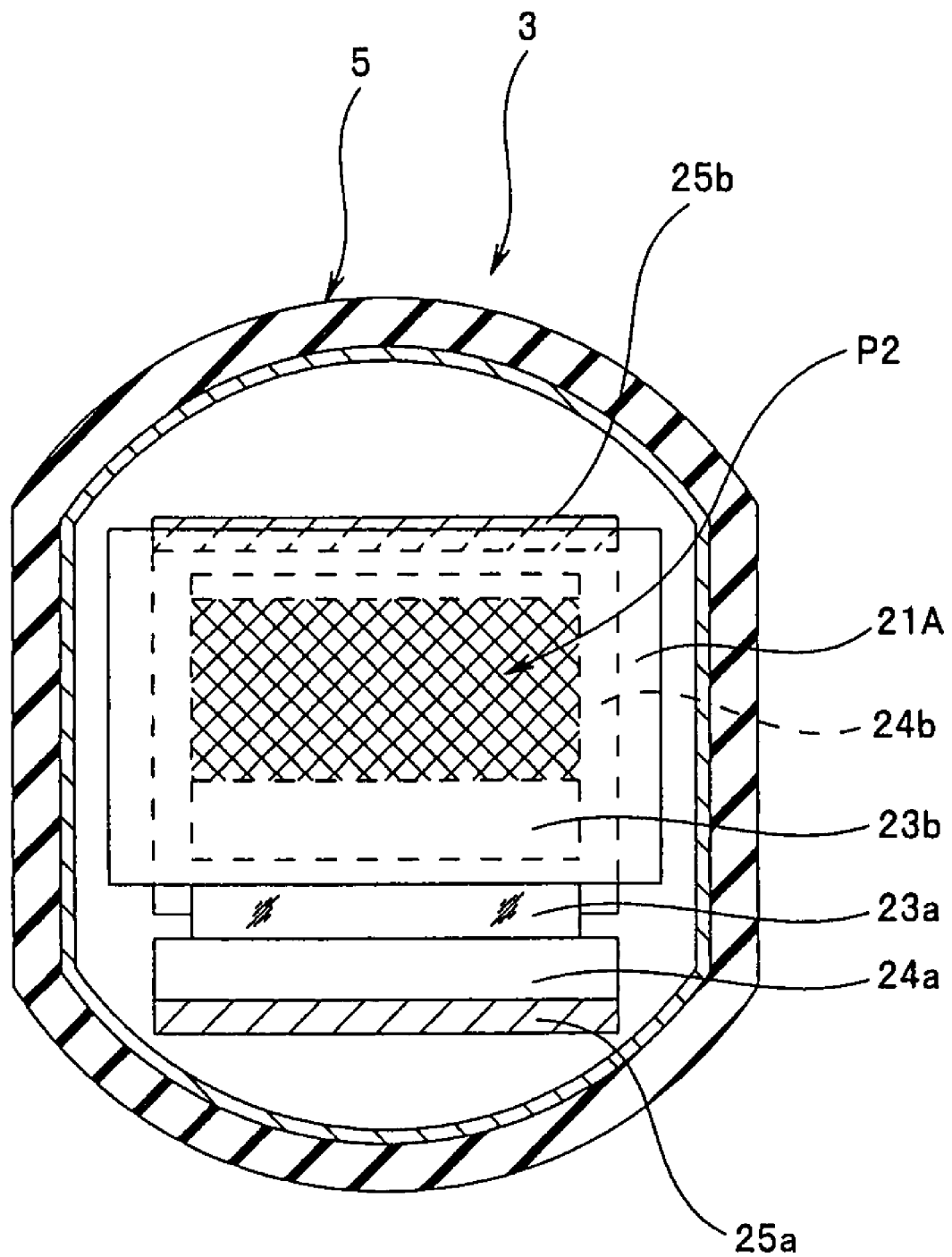
FIG. 12 is a sectional view of the distal end portion taken along line XII-XII in FIG. 11.

FIGS. 9 to 12 relate to Embodiment 3 of the present invention. FIG. 9 is a partial enlarged sectional view showing a part of a conventional image pickup apparatus, that is, a distal end portion of the image pickup apparatus, and illustrating problems with the image pickup apparatus. FIG. 10 is a partial sectional view of the distal end portion taken along line X-X in FIG. 9. FIG. 11 is a partly enlarged partial sectional view showing a part of an image pickup apparatus in an endoscope in accordance with Embodiment 3, that is, a distal end portion of the image pickup apparatus. FIG. 12 is a sectional view of the distal end portion taken along line XII-XII in FIG. 11.

In Embodiment 3, shown in FIGS. 9 to 12, components similar to those of the image pickup apparatus 5 in the endoscope 1 in accordance with Embodiment 1 are denoted by the same reference numerals and will not be described below. Description will be given below of only the components different from those of the image pickup apparatus 5 in the endoscope 1 in accordance with Embodiment 1.

The endoscope 1 is required to have the insertion portion 2 of a reduced diameter and to provide an improved image quality. However, for some applied sites, the endoscope 1 is inserted into the applied site using an endoscope insertion aid (not shown) called a trocar and designed to insert the endoscope 1.

In this case, the thicker insertion portion 2 of the endoscope 1 cannot be inserted into the trocar. Consequently, the diameter of the distal end portion 3 of the insertion portion 2 of the endoscope 1 needs to be set to allow the distal end portion 3 to be inserted into the trocar.

If the solid-state image pickup device is originally assumed to use the trocar, the solid-state image pickup devices 24a and 24b in the image pickup apparatus 5 in the endoscope 1 are provided in the distal end portion 3 so as to reduce the diameter of the distal end portion 3. However, if a general-purpose solid-state image pickup device used for other image pickup instruments or the like is provided in the distal end portion 3, the use of the trocar is not taken into account. This makes it difficult to reduce the diameter of the distal end portion 3. Thus, a configuration will be shown below which enables a reduction in the diameter of the distal end portion 3 even if the general-purpose solid-state image pickup device is used.

If the image pickup unit 23 of the image pickup apparatus 5 is configured using the general-purpose first and second solid-state image pickup devices 24a and 24b as shown in FIG. 9, since the second solid-state image pickup device 24b normally uses all the pixels in the effective pixel area (area P1 shown in FIG. 10) as shown in FIG. 10, the optical axis of the objective optical system unit 12 needs to be aligned with the center of the effective pixel area P1 of the second solid-state image pickup device 24b.

This increases the height h1 (see FIG. 9) of the second solid-state image pickup device 24b from the optical axis and thus the thickness of the image pickup apparatus 5. This results in an increase in the diameter of the distal end portion 3 of the insertion portion 2.

Thus, Embodiment 3 makes improvements such that the number of pixels used in the second solid-state image pickup device 24b is reduced even if the general-purpose first and second solid-state image pickup devices 24a and 24b are used. This in turn enables a reduction in the size of the image pickup apparatus 5 and the distal end portion 3 of the insertion portion 2.

Specifically, the image pickup apparatus 5 in the endoscope 1 in accordance with Embodiment 3 is configured substantially similarly to that in accordance with Embodiment 1 as shown in FIGS. 11 and 12. However, at least one of the first and second solid-state image pickup devices 24a and 24b is placed so that the optical axis of the objective optical system unit 12 is offset from the center of the effective pixel area P1 of the at least one of the first and second solid-state image pickup devices 24a and 24b.

That is, the image pickup apparatus 5 is configured such that the first solid-state image pickup device 24a or the second solid-state image pickup device 24b is stuck to the prism 21 at a position different from that in Embodiment 1.

As shown in FIG. 9, the conventional technique aligns the optical axis of the objective optical system unit 12 with the center of the effective pixel area P1 of the second solid-state image pickup device 24b.

However, in the image pickup apparatus 5 in Embodiment 3, in order to minimize a space S shown in FIG. 9, the second solid-state image pickup device 24b is shifted in the direction of an arrow to the extent that the second solid-state image pickup device 24b does not contact the first solid-state image pickup device 24a as shown in FIGS. 11 and 12.

Shifting the second solid-state image pickup device 24b toward the first solid-state image pickup device 24a reduces the range of light reception condensed by the objective optical system unit 12. All the pixels used are located in an effective pixel area P2 shown in FIG. 13; the effective pixel area P2 is smaller than the effective pixel area P1, shown in FIG. 10.

However, the second solid-state image pickup device 24b can be placed at a height h2 (see FIG. 11) lower than the height h1 (see FIG. 9) of the second solid-state image pickup device 24b from the objective optical system unit 12 by Δh2.

In Embodiment 3, the positions of the pixels used in the first solid-state image pickup device 24a are different from those of the pixels used in the second solid-state image pickup device 24b. However, this may be resolved by the image processing section in the video processor by executing image processing such that an image in the first solid-state image pickup device 24a matches an image in the second solid-state image pickup device 24b.

Further, in order to minimize the space S shown in FIG. 9, the first solid-state image pickup device 24a may be shifted to the extent that the first solid-state image pickup device 24 does not contact the second solid-state image pickup device 24b.

This case is the same as that of the second solid-state image pickup device 24b. That is, all the pixels used in the first solid-state image pickup device 24a are located in the effective pixel area P2, shown in FIG. 12; the effective pixel area P2 is smaller than the effective pixel area P1, shown in FIG. 10. However, the first solid-state image pickup device 24a can be placed at a position Δh2 closer to the second solid-state image pickup device 24b from the optical axis of the objective optical system unit 12. This enables a reduction in the length of the image pickup unit 23 in the direction of the optical axis of the objective optical system unit 12.

The other configuration and working of Embodiment 3 are similar to those of Embodiment 1.

Consequently, Embodiment 3 can exert effects similar to those of Embodiment 1. Furthermore, if the diameter of the distal end portion 3 of the insertion portion 2 needs to be reduced in association with the use of the trocar, Embodiment 3 can reduce the height of the second solid-state image pickup device 24b from the optical axis of the objective optical system unit 12 by shifting the second solid-state image pickup device 24b toward the first solid-state image pickup device 24a by a predetermined amount, in spite of an associated reduction in the number of pixels used in the second solid-state image pickup device 24b. This enables a reduction in the size of the image pickup apparatus 5 and the diameter of the distal end portion 3 of the insertion portion 2. As a result, the trocar can be used.

In Embodiments 1 to 3 in accordance with the present invention, the endoscope 1 having the image pickup apparatus 5 the size of which can be reduced has been described. However, the present invention is not limited thereto but is applicable to other image pickup instruments other than the endoscope which has an image pickup apparatus desired to have a reduced size and a reduced diameter.

The present invention, for which the embodiments have been described above, is not limited to the embodiments. In implementation, many variations may be made to the embodiments without departing from the spirit of the present invention. Moreover, the embodiments include various levels of inventions and various inventions can be extracted by appropriately combining a plurality of the disclosed components.

For example, even though any of the components shown in the embodiments are removed, if the object described in BACKGROUND OF THE INVENTION can be satisfied and the above-described effects described can be achieved, the configuration free from the components can be extracted as the inventions.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope including a prism having a first prism and a second prism that are joined together so as to divide and emit incident light having passed through an objective optical system into two optical paths, a first solid-state image pickup device that is provided along an optical axis direction of the objective optical system and receives light emitted by the prism in a direction perpendicular to the optical axis direction after being reflected by an interface between the first prism and the second prism, and a second solid-state image pickup device that is provided along the direction perpendicular to the optical axis direction and receives light emitted by the prism along the optical axis direction after passing through the first and second prisms, the endoscope comprising:

a first connection portion provided on a first side surface of the first solid-state image pickup device, the first side surface located on a side of the first solid-state image pickup device which is closer to the objective optical system and parallel to the direction perpendicular to the optical axis direction, and the first connection portion connecting the first solid-state image pickup device to a first circuit board; and a second connection portion provided on a second side surface of the second solid-state image pickup device, the second side surface located at a position in the second solid-state image pickup device that is furthest from the first connection portion in the direction perpendicular to the optical axis direction and parallel to the optical axis direction, and the second connection portion connecting the second solid-state image pickup device to a second circuit board, wherein the first solid-state image pickup device and the second solid-state image pickup device are arranged so that a third side surface of the first solid-state image pickup device that is opposite to the first side surface in the optical axis direction faces toward and in proximity to a fourth side surface of the second solid-state image pickup device which is opposite to the second side surface in the direction perpendicular to the optical axis direction.

2. The endoscope according to claim 1, wherein the third side surface of the first solid-state image pickup device is provided at a position such that a distance from an effective pixel area in the first solid-state image pickup device to an outer peripheral end in the first solid-state image pickup device is minimized in a surface including the effective pixel area and the fourth side surface of the second solid-state image pickup device is provided at a position such that a distance from an effective pixel area in the second solid-state image pickup device to an outer circumference of the second solid-state image pickup device is minimized in a surface including the effective pixel area.

3. The endoscope according to claim 1, wherein the first solid-state image pickup device and the second solid-state image pickup device are arranged surface-symmetrically with respect to the interface between the first prism and the second prism.

4. The endoscope according to claim 2, wherein the first solid-state image pickup device and the second solid-state image pickup device are arranged surface-symmetrically with respect to the interface between the first prism and the second prism.

5. The endoscope according to claim 1, wherein a center of the effective pixel area in at least one of the first solid-state image pickup device and the second solid-state image pickup device is offset from an optical axis of the objective optical system.

6. The endoscope according to claim 2, wherein a center of the effective pixel area in at least one of the first solid-state image pickup device and the second solid-state image pickup device is offset from an optical axis of the objective optical system.

7. The endoscope according to claim 3, wherein a center of the effective pixel area in at least one of the first solid-state image pickup device and the second solid-state image pickup device is offset from an optical axis of the objective optical system.

8. The endoscope according to claim 4, wherein a center of the effective pixel area in at least one of the first solid-state image pickup device and the second solid-state image pickup device is offset from an optical axis of the objective optical system.

9. An endoscope apparatus comprising an endoscope including a prism having a first prism and a second prism that are joined together so as to divide and emit incident light having passed through an objective optical system into two optical paths, a first solid-state image pickup device that is provided along an optical axis direction of the objective optical system and receives light emitted by the prism in a direction perpendicular to the optical axis direction after being reflected by an interface between the first prism and the second prism, and a second solid-state image pickup device that is provided along the direction perpendicular to the optical axis direction and receives light emitted by the prism after passing through the first and second prisms, the endoscope apparatus comprising:

a first connection portion provided on a first side surface of the first solid-state image pickup device, the first side surface located on a side of the first solid-state image pickup device that is closer to the objective optical system and parallel to the direction perpendicular to the optical axis direction, and the first connection portion connecting to connect the first solid-state image pickup device to a first circuit board; and a second connection portion provided on a second side surface of the second solid-state image pickup device, the second side surface located at a position in the second solid-state image pickup device that is furthest from the first connection portion in the direction perpendicular to the optical axis direction and parallel to the optical axis direction, and the second connection portion connecting the second solid-state image pickup device to a second circuit board, wherein the first solid-state image pickup device and the second solid-state image pickup device are arranged so that a third side surface of the first solid-state image pickup device, that is opposite to the first side surface in the optical axis direction, faces toward and in proximity to a fourth side surface of the second solid-state image pickup device which is opposite to the second side surface in the direction perpendicular to the optical axis direction.

* * * * *